United States Patent
Kobayashi et al.

(10) Patent No.: US 7,384,646 B2
(45) Date of Patent: Jun. 10, 2008

(54) ANTISEPTIC DISINFECTANT, AND COSMETICS AND TOILETRIES, MEDICINE OR FOOD CONTAINING THE SAME

(75) Inventors: Aki Kobayashi, Kyoto (JP); Hiroya Okamoto, Osaka (JP); Fumihiro Okada, Osaka (JP)

(73) Assignee: Mandom Corporation, Osaka (JP)

(*) Notice: Subject to any disclaimer, the term of this patent is extended or adjusted under 35 U.S.C. 154(b) by 517 days.

(21) Appl. No.: 10/500,355

(22) PCT Filed: Sep. 25, 2003

(86) PCT No.: PCT/JP03/12287

§ 371 (c)(1),
(2), (4) Date: Jun. 30, 2004

(87) PCT Pub. No.: WO2004/028519

PCT Pub. Date: Apr. 8, 2004

(65) Prior Publication Data

US 2005/0182142 A1 Aug. 18, 2005

(30) Foreign Application Priority Data

Sep. 26, 2002 (JP) .............................. 2002-281677

(51) Int. Cl.
*A01N 25/00* (2006.01)
*A61K 31/12* (2006.01)
*A61K 31/11* (2006.01)
*A61K 31/045* (2006.01)

(52) U.S. Cl. .................. 424/405; 514/688; 514/699; 514/729; 514/738

(58) Field of Classification Search .............. 514/688, 514/699, 738, 729; 404/405
See application file for complete search history.

(56) References Cited

U.S. PATENT DOCUMENTS

| | | | |
|---|---|---|---|
| 2,550,255 A | 4/1951 | Jensen | |
| 5,403,587 A | 4/1995 | McCue et al. | |
| 5,630,847 A | 5/1997 | Roetker | |
| 6,348,187 B1 | 2/2002 | Pan et al. | |
| 2001/0036964 A1 | 11/2001 | Clarkson et al. | |

2004/0123775 A1 7/2004 Ono et al.

FOREIGN PATENT DOCUMENTS

| EP | 587002 | 3/1994 |
|---|---|---|
| JP | 59-175423 | 10/1984 |
| JP | 04304887 A * | 10/1992 |
| JP | 5-67608 | 9/1993 |
| JP | 10-053510 | 2/1998 |
| JP | 11-193208 | 7/1999 |
| JP | 11-310506 | 11/1999 |
| JP | 11-322591 | 11/1999 |
| JP | 2001-048720 | 2/2001 |
| JP | 2001-48781 | 2/2001 |
| JP | 2001-302475 | 10/2001 |
| JP | 2002-206097 | 7/2002 |
| JP | 2003-81736 | 3/2003 |
| JP | 2003-300811 | 10/2003 |
| JP | 2004-010497 | 1/2004 |

OTHER PUBLICATIONS

Kim et al. Antibacterial activity of some essential oil components against five foodborne pathogens. J. Argric, Food Chem. 1995, 43, pp. 2839-2845.*
Kurita et al., "Synergistic Antimicrobial Effect of Sodium Chloride and Essential Oil Components", Agricultural and Biological Chemistry, vol. 46, No. 1, 1982, pp. 159-166 XP009089993.
Professor Dr. Hildebert Wagner, "Pharmazeutische Biologie Drogen und ihre Inhaltsstoffe" Gustav Fischer Verlag, Stuttgart, 1988 XP002452582.
Supplementary European Search Report dated Nov. 20, 2007.

* cited by examiner

*Primary Examiner*—Jennifer Kim
(74) *Attorney, Agent, or Firm*—Westerman, Hattori, Daniels & Adrian, LLP.

(57) ABSTRACT

The purpose of the present invention is to provide antiseptic disinfectant, and cosmetics and toiletries, medicine or food containing the same, which enhance the antibacterial activity that 1,2-alkanediol originally have against a broad range of strains by compounding 1,2-alkanediol with 5-10 carbons and a certain fragrance component.

The present invention relates to an antiseptic disinfectant, and cosmetics and toiletries, medicine or food containing the same, which include 1,2-alkanediol with 5-10 carbons, and one or more materials selected from a group of citral, geraniol, nerol, perillaldehyde, α-terpineol, dodecanol and L-carvone.

4 Claims, 10 Drawing Sheets

(a) MIC as to E.coli (μg/ml)

(b) MIC as to S.aureus (μg/ml)

(c) MIC as to C.albicans (μg/ml)

(d) MIC as to A.niger (μg/ml)

FIG.4

(a) MIC as to E.coli (μ g/ml)

(b) MIC as to S aureus (μ g/ml)

(c) MIC as to C.albicans (μ g/ml)

(d) MIC as to A.niger (μ g/ml)

FIG.5

(a) MIC as to E.coli (μg/ml)

(b) MIC as to S.aureus (μg/ml)

(c) MIC as to C.albicans (μg/ml)

(d) MIC as to A.niger (μg/ml)

FIG.6

(a) MIC as to P.aeruginosa (μ g/ml)

(b) MIC as to S.aureus (μ g/ml)

(c) MIC as to C.albicans (μ g/ml)

(d) MIC as to A.niger (μ g/ml)

FIG.7

(a) MIC as to P.aeruginosa (μ g/ml)

(b) MIC as to S.aureus (μ g/ml)

(c) MIC as to C.albicans (μ g/ml)

(d) MIC as to A.niger (μ g/ml)

FIG.8

(a) MIC as to P.aeruginosa (μ g/ml)

(b) MIC as to S.aureus (μ g/ml)

(c) MIC as to C.albicans (μ g/ml)

(d) MIC as to A.niger (μ g/ml)

FIG.9

(a) MIC as to E.coli (μ g/ml)

(b) MIC as to S.aureus (μ g/ml)

(c) MIC as to C.albicans (μ g/ml)

(d) MIC as to A.niger (μ g/ml)

(e) MIC as to P.aeruginosa (μ g/ml)

FIG.10

(a) MIC as to E.coli (μ g/ml)

(b) MIC as to S.aureus (μ g/ml)

(c) MIC as to C.albicans (μ g/ml)

(d) MIC as to A.niger (μ g/ml)

(e) MIC as to P.aeruginosa (μ g/ml)

US 7,384,646 B2

ANTISEPTIC DISINFECTANT, AND COSMETICS AND TOILETRIES, MEDICINE OR FOOD CONTAINING THE SAME

TECHNICAL FIELD

The present invention relates to an antiseptic disinfectant, and cosmetics and toiletries, medicine or food containing the same. The purpose of the present invention is to provide the antiseptic disinfectant, and cosmetics and toiletries, medicine or food containing the same which enhance the antibacterial activity that 1,2-alkanediol originally have against a broad range of strains by compounding 1,2-alkanediol with 5-10 carbons and a certain fragrance component.

TECHNICAL BACKGROUND

Paraben, benzoic acid, salicylic acid and so on have been used for the antiseptic disinfectants in the cosmetics and toiletries (including quasi drugs), medicine or food. As the above-mentioned conventional antiseptic disinfectants have low degree in their safety because of the high skin irritant etc., they have a defect that the range of the concentration for use tends to be limited. For example, the restricted concentration of paraben and benzoate for use is 1%, and the restricted concentration of benzoic acid and salicylic acid for use is 0.2%. Further, there have been problems that the antiseptic disinfection effect of those antiseptic disinfectants is not reliable because they are easily influenced by pH, and that antiseptic and antibacterial activity may remarkably fall by the combination use with other compounds such as surfactant. Still further, the number of people who are allergic to those antiseptic disinfectants is increasing in recent years. Therefore, more people are oriented to the safety, and so the demand for the cosmetics and toiletries, medicine and food without the antiseptic disinfectant or containing very reduced amount of it is increasing.

As the technical means to reduce or remove the antiseptic disinfectant, the antiseptic disinfectant containing 1,2-alkanediol (referring to publication No. 11-322591 of Published Japanese patent application) and moisturizing bacteriostatic for detergent or nondetergent cosmetics and toiletries containing 1,2-octanediol (referring to publication No. 2001-48720 of Published Japanese patent application) are disclosed. In using 1,2-alkanediol such as 1,2-octanediol solely for the antiseptic disinfectant, 1,2-alkanediol has to be compounded in a large amount if the nonionic surfactant exists in the compound. Further, as the 1,2-alkanediol has a peculiar odor of its material, it causes the problem of the odor when compounded in cosmetics and toiletries, etc.

Still further, for the technical means as to the antiseptic disinfectant using 1,2-alkanediol, a composition for external use compounded with 1,2-pentanediol and 2-phenoxyethanol (referring to publication No. 10-53510 of Published Japanese patent application) and an antiseptic disinfectant containing 1,2-alkanediol and paraben (referring to publication No. 11-310506 of Published Japanese patent application) are disclosed. The aims of those are, however, to improve the effect of antiseptic by the combination use of antiseptic and 1,2-alkanediol such as 1,2-pentanediol, but not to completely remove the antiseptic itself.

Meanwhile, fragrance compositions are generally compounded in the cosmetics and toiletries and food etc. to give rich smell to the products. It is known since a long time ago that the fragrance compositions theirselves have antibacterial action, and for example, the fragrance composition such as cresyl acetate, methyl eugenol, heliotropin and ethyl salicylate is disclosed as anticaries that has antibacterial action against mutans (referring to Published Japanese patent publication No. 5-67608). However, there has been a problem that the antibacterial action only by the fragrance composition does not give enough antiseptic disinfectant effect for cosmetics, toiletries and so on.

In view of the above-mentioned circumstances, the inventors, after studying very hard, found that combination use of 1,2-alkanediol and a specific fragrance composition enhances the antibacterial activity which 1,2-alkanediol originally has against many different kinds of strains to mask the odor of 1,2-alkanediol material, thereby the present invention has been completed.

DISCLOSURE OF THE INVENTION

The invention described in claim 1 relates to an antiseptic disinfectant which includes 1,2-alkanediol with 5-10 carbons, and one or more materials selected from a group of citral, geraniol, nerol, perillaldehyde, α-terpineol, dodecanol and L-carvone.

The invention described in claim 2 relates to an antiseptic disinfectant described in claim 1 characterized in that the 1,2-alkanediol is 1,2-hexanediol and/or 1,2-octanediol.

The invention described in claim 3 relates to an antiseptic disinfectant described in claim 1 characterized in that the 1,2-alkanediol is 1,2-octanediol.

The invention described in claim 4 relates to cosmetics and toiletries including the antiseptic disinfectant described in claim 1.

The invention described in claim 5 relates to cosmetics and toiletries including the antiseptic disinfectant described in claim 2.

The invention described in claim 6 relates to cosmetics and toiletries including the antiseptic disinfectant described in claim 3.

The invention described in claim 7 relates to medicine including the antiseptic disinfectant described in claim 1.

The invention described in claim 8 relates to medicine including the antiseptic disinfectant described in claim 2.

The invention described in claim 9 relates to medicine including the antiseptic disinfectant described in claim 3.

The invention described in claim 10 relates to a food including the antiseptic disinfectant described in claim 1.

The invention described in claim 11 relates to a food including the antiseptic disinfectant described in claim 2.

The invention described in claim 12 relates to a food including the antiseptic disinfectant described in claim 3.

BEST MODE FOR CARRYING OUT THE INVENTION

Hereinafter, the antiseptic disinfectant of the present invention is disclosed in detail. The antiseptic disinfectant of the present invention contains 1,2-alkanediol with 5-10 carbons, and one or more materials selected from a group of citral, geraniol, nerol, perillaldehyde, α-terpineol, dodecanol and L-carvone.

The first component of the antiseptic disinfectant of the present invention is 1,2-alkanediol with 5-10 carbons as indicated in the following chemical formula 1, and more specifically, it can be 1,2-pentanediol, 1,2-hexanediol, 1,2-heptanediol, 1,2-octanediol, 1,2-nonanediol, or 1,2-decanediol.

(Formula 1)

("n" in the formula represents integer 2-7)

In the present invention, one of the above-mentioned 1,2-alkanediols can be used solely, or two or more of those can be compounded.

1,2-alkanediol itself has a fine antibacterial activity, and takes effect of enhancing the antibacterial activity of the antiseptic disinfectant. Especially, in the present invention, it is preferable to use 1,2-hexanediol or 1,2-octanediol out of 1,2-alkanediols with 5-10 carbons as they have superior antibacterial activity against Eumycetes such as bacteria, yeast, Fungi and so on. It would be more preferable to use 1,2-octanediol.

The second component of the antiseptic disinfectant of the present invention is one or more materials selected from a group of citral, geraniol, nerol, perillaldehyde, α-terpineol, dodecanol and L-carvone.

The second component is the aromatic material which not only masks the peculiar odor of 1,2-alkanediol but also enhances the antibacterial activity.

Citral has a molecular formula of $C_{10}H_{16}O$, and is contained in vegetable oil such as lemon grass oil and lemon oil. Citral has two stereoisomers of geranial (transform) and neral (cis form), and either one of them or the mixture of them can be used.

Geraniol has a molecular formula of $C_{10}H_{18}O$, and is contained in vegetable oil such as palmarosa oil, rose oil and Geranium oil.

Nerol has a molecular formula of $C_{10}H_{18}O$, and is contained in vegetable oil such as neroli oil and rose oil.

Perillaldehyde has a molecular formula of $C_{10}H_{14}O$, and is essence oil of Labiatae plants. In the present invention, Each of d-perillaldehyde, L-perillaldehyde and dL-perillaldehyde can be suitably used.

α-terpineol has a molecular formula of $C_{10}H_{18}O$, and is contained in vegetable oil such as turpentine oil, cardamom oil and orange oil.

Dodecanol is monohydric alcohol with 12 carbons, which has a molecular formula of $C_{12}H_{26}O$.

L-carvone has a molecular formula of $C_{10}H_{14}O$, and is a principal component of spearmint oil which is a essence oil of Labiatae plants. L-carvone has an odor of spearmint.

In the present invention, one material from a group of citral, geraniol, nerol, perillaldehyde, α-terpineol, dodecanol and L-carvone can be used solely, or two or more of those can be compounded.

In the antiseptic disinfectant of the present invention, the content of both of the first component 1,2-alkanediol with 5-10 carbons and the second component fragrance compositions are not limited, but it would be preferred that they are compounded to satisfy the weight ratio to be between 0.5:1 and 100:1, more preferably between 1:1 and 10:1. It is not preferable to compound 1,2-alkanediol over 100 times as much as fragrance components by weight because the effect of enhancing antibacterial activity cannot be expected in the condition, while it is not preferable to compound 1,2-alkanediol under 0.5 times as much by weight because the aromatic odor increases too much in the condition.

The antiseptic disinfectant includes 1,2-alkanediol with 5-10 carbons as the first component, and one or more materials selected from a group of citral, geraniol, nerol, perillaldehyde, α-terpineol, dodecanol and L-carvone as the second component, it masks the raw material odor of 1,2-alkanediol. At the same time, fine antiseptic disinfectant activity against bacteria, yeast, fungi and so on can be shown because of the multiplier effect by the first and second components as indicated in the test mentioned below. Consequently, it is not necessary to compound the conventional antiseptic disinfectant such as paraben, benzoic acid and salicylic acid, thereby the high level of safety is secured.

The above-mentioned antiseptic disinfectant of the present invention can be used for the composition of cosmetics and toiletries, medicine, or food.

Specifically, it can be preferably used for skin cosmetics and toiletries such as facial cleansing, skin lotion, emulsion, cream, foundation, mascara, nail enamel and rouge, for hair cosmetics and toiletries such as shampoo, hair treatment, hair growth stimulant, hair cream, hair lotion, hair foam, permanent wave agent, for medicinal cosmetics (quasi drugs) for a definite purpose such as chloasma or ephelides, for medicine such as curative medicine for acne, collutorium or troches, and further for food such as chewing gums, candies or beverages.

In preparing cosmetics and toiletries, medicine or food with the antiseptic disinfectant of the present invention, the compositions which are usually contained in the cosmetics, toiletries, medicine or food can optionally be compounded within the amount that does not spoil the effect of the present invention. For example, fat, cere, higher fatty acid, lower alcohol, higher alcohol, sterol, fatty acid ester, humectant, surfactant, high molecular compound, inorganic pigment, coloring matter, fragrance composition, antioxidant, ultraviolet absorber, vitamin, astringent, skin whitening agent, extract from animals and plants, sequestering agent, purified water and so on would be enumerated for cosmetics, toiletries or medicine (including quasi drugs).

As to food, oil of animals and plants, polysaccharide, sweetener, food color, gum base and so on can be enumerated for example.

In preparing cosmetics, toiletries, medicine or food, the content of the antiseptic disinfectant is not limited, but the composition contains 0.01-20 percent by weight of the antiseptic disinfectant, and, more preferably, contains 0.05-5 percent by weight of it. If more than 20 percent by weight of the antiseptic disinfectant is contained, additional effect would not be expected. While, if contained under 0.01 percent by weight, it would not be preferable because the enough antibacterial effect cannot be obtained.

EMBODIMENT

Embodiment 1

*Escherichia coli* IFO3972 of Gram-negative bacteria, *Staphylococcus aureus* IFO13276 (*Staphylococcus aureus*) as Gram-positive bacteria, *Candida albicans* IFO1594 (mycotic stomatitis) as yeast, and *Aspergillus niger* IFO9455 as Fungus are used as sample bacterias.

(Preparation of Bacteria)

For preparing bacteria, as to *Escherichia coli* and *Staphylococcus aureus*, they are incubated at 35° C. in the agar medium, and further incubated at 35° C. after transferred into the bouillon medium. The bacteria is prepared by diluting the obtained culture solution to about $10^8$ cell/ml.

As to yeast (*Candida albicans*), the bacteria is prepared by incubating the yeast in the same way as *Escherichia coli* and *Staphylococcus aureus* at 30° C. and diluting the yeast to about $10^7$ cell/ml.

As to Fungus, the bacteria is prepared by incubating the fungus at 25° C., suspending its sporozoite into the physiologocal saline with 2% of Tween 80 (polyoxyethylene (20)sorbitan Monoleate) and diluting it to about $10^6$ cell_/ml.

Preparation of Diluting Series of the Test Material

With a dilution solvent of ethyl cellosolve of 20 w/w %, 1,2-octanediol solution of 5, 4, 3, 2.5, 2.25, 2, 1.75, 1.5, 1.25 and 1 w/v % are prepared.

While, as to citral and the 50:50 by weight mixture of 1,2-octanediol and citral, the dilution series are prepared by doubling diluting the 10 w/v % solution.

Measurement of Minimum Inhibitory Concentration (MIC)

1 ml of the above-mentioned dilution series including the test material and 9 ml of the agar medium are introduced to each schales, and the above-mentioned inoculating bacteria was applied on each of the schales at the length of 1 cm. *Escherichia coli* and *Staphylococcus aureus* and *Pseudomonas* were incubated at 35° C., and it was judged whether or not the bacteria had grown two days later. The yeast and Fungus were incubated at 25° C., and it was judged whether or not the bacteria had grown three days later. The minimum concentration in which the bacteria did not grow is MIC.

Still more, antibacterial activity can be evaluated by the MIC. When the concentration of the test material is low, it does not effect the microbes. As the concentration gets higher, growth inhibition occurs. Further, as the concentration gets higher, the growth inhibition progresses, eventually to stop growth. The concentration at the point is shown as MIC. Accordingly, when the concentration goes above MIC, microbes die.

Evaluation of Dual Minimum Inhibitory Concentration

Each MIC of the obtained 1,2-octanediol, citral, and the 50:50 mixture by weight of 1,2-octanediol and citral corresponding the compounding amount of 1,2-octanediol and citral is plotted to make out the dual minimum inhibitory concentration. Action and effect in case that two kinds of antibacterial materials are compounded can be judged by the dual minimum inhibitory concentration. More specifically, the actions caused by compounding two antibacterial materials are roughly classified into synergistic action, additive action and counteraction. Synergistic action is the action in that two kinds of agent act synergistically, to enhance the antibacterial activity that the agents originally have. The additive action is the action in that the antibacterial activities of the agents are put together. The counteraction is the action in that one agent cancels the antibacterial activity of the other agent.

Figure 1:
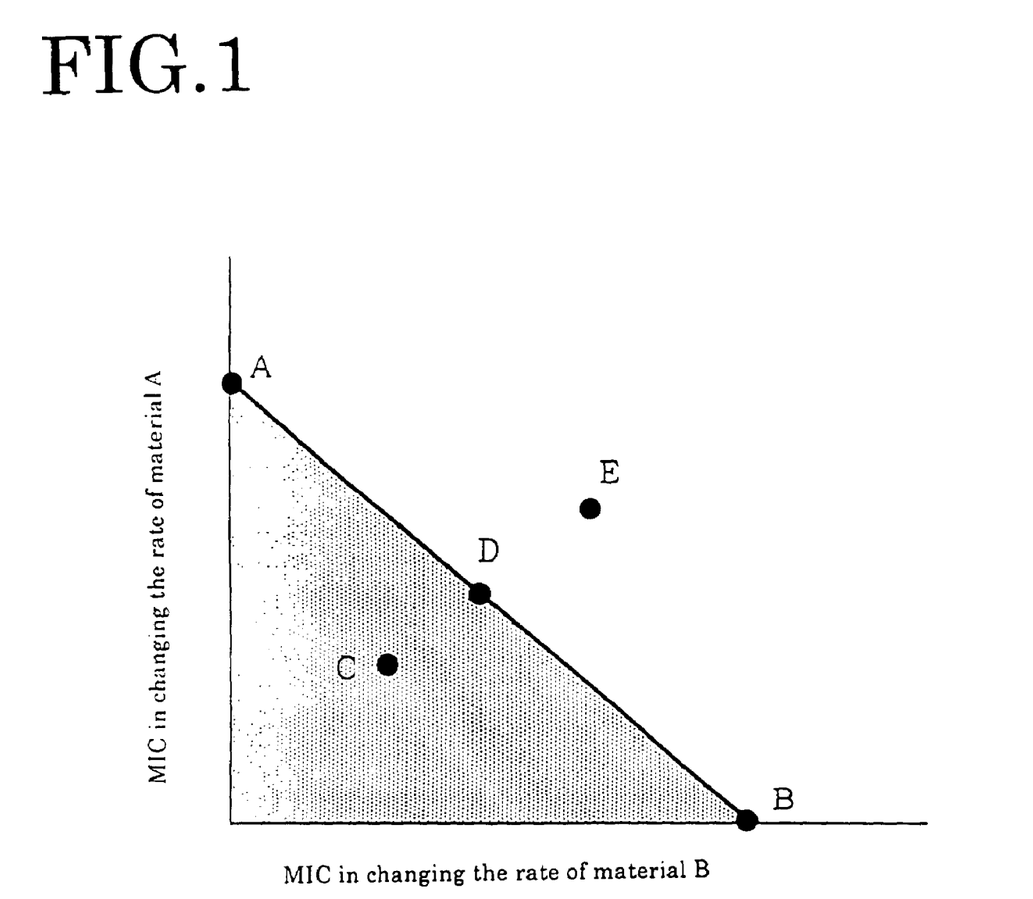
FIG. 1 is a diagram showing an example of a method to determine the effect of compounding two antibacterial materials by means of dual minimum inhibitory concentration.

The method using dual minimum inhibitory concentration, as shown in FIG. 1 for example, is the method to measure MICs as to material A and Material B at different proportions of them and to judge the result in view of the graph. In this method, a line is drawn to connect MIC (point A) in using only material A to MIC (point B) in using only material B. When the MIC (point C) in using both materials is inside the line, it is judged to be Synergistic action that antibacterial activity was strengthened by the combined use. When the MIC (point D) is on the line, it can be judged to be the additive action. When the MIC (point E) is in the outside of the line, it is judged to be the counteraction that cancels antibacterial activity of one or both of the materials to decrease the antibacterial activity.

Figure 2:
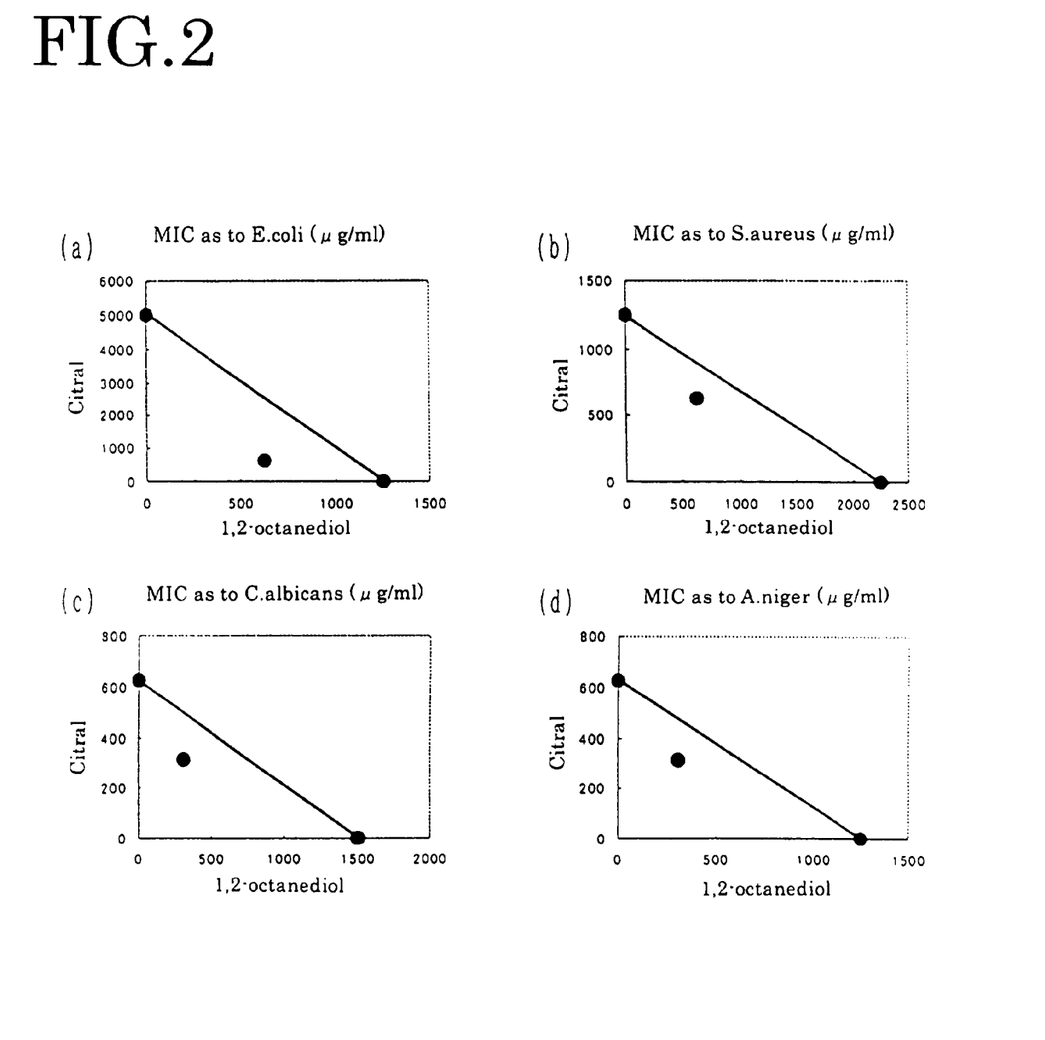
FIG. 2 is dual minimum inhibitory concentration diagrams as to citral.
Figure 3:
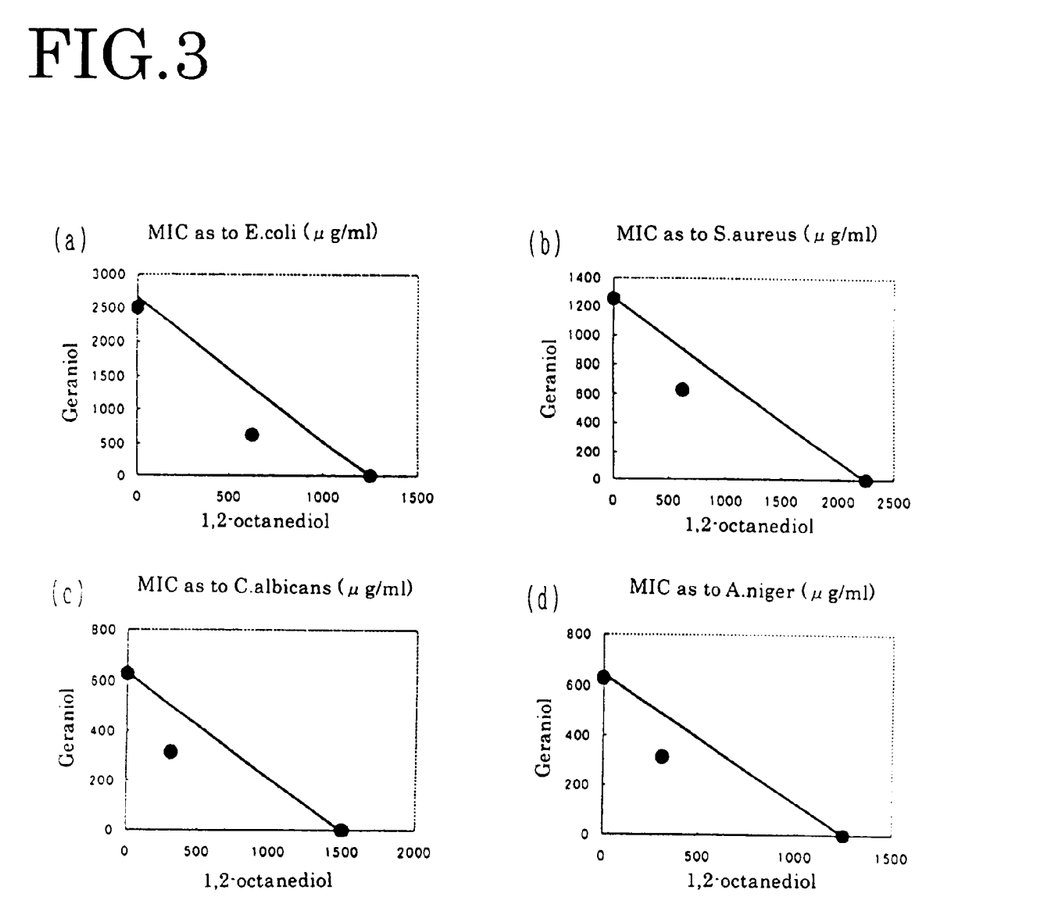
FIG. 3 is dual minimum inhibitory concentration diagrams as to geraniol.
Figure 4:
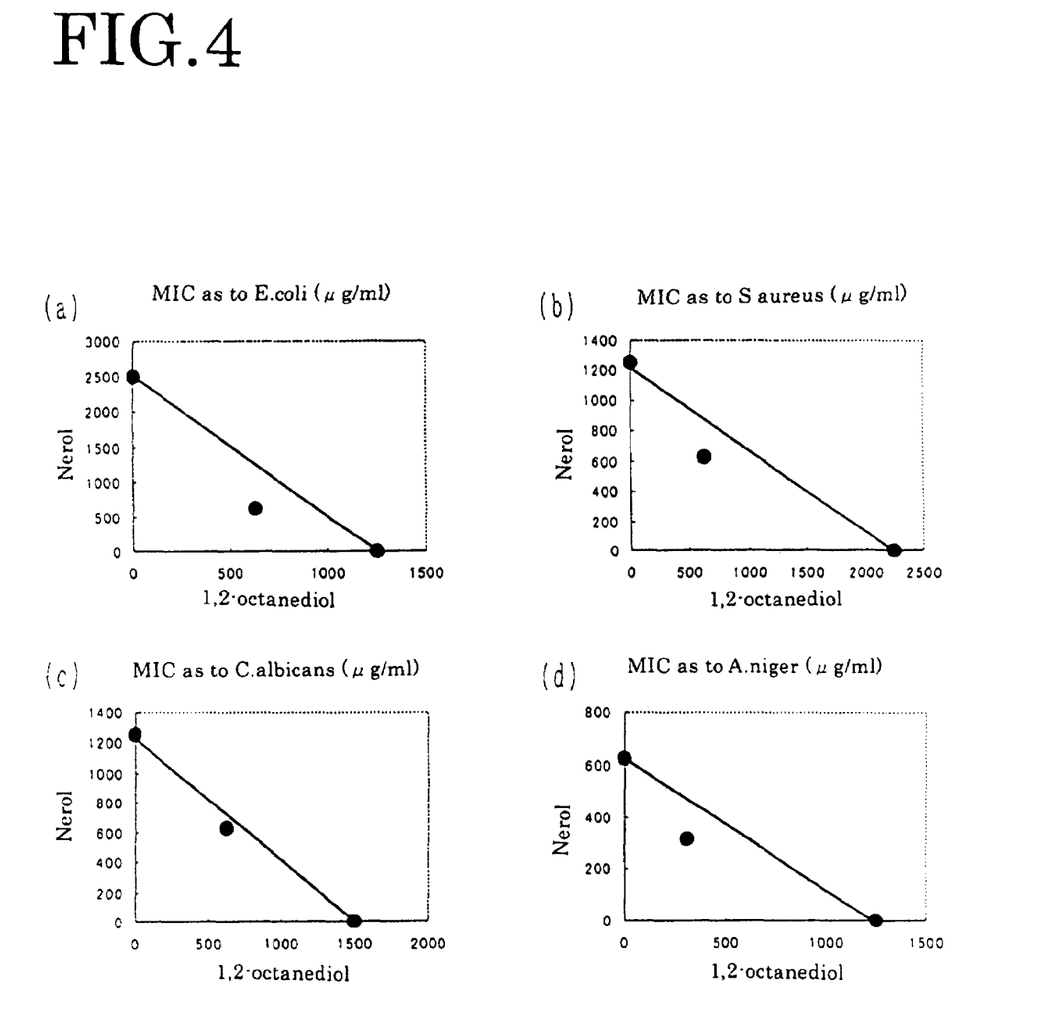
FIG. 4 is dual minimum inhibitory concentration diagrams as to nerol.
Figure 5:
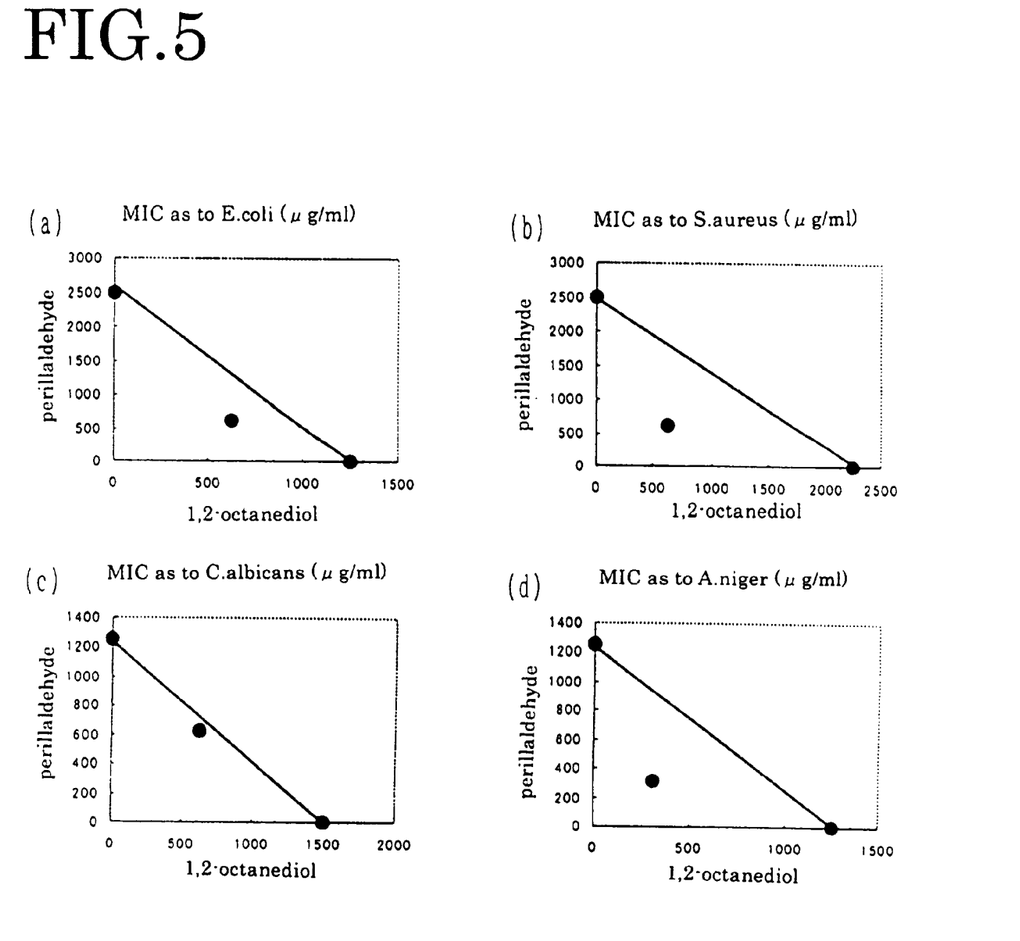
FIG. 5 is dual minimum inhibitory concentration diagrams as to perillaldehyde.

The dual minimum inhibitory concentration diagram as to the citral is shown in FIG. 2.

Evaluation of the Antibacterial Effect

The antibacterial effect in the case of mixing 1,2-octanediol and citral was evaluated by the following evaluation criterion from dual minimum inhibitory concentration diagram in FIG. 2. The result is described in the table 1.

Evaluation Criterion

◯: There is synergistic action in the antibacterial effect.

Δ: There is additive action in the antibacterial effect.

x: There is counteraction in the antibacterial effect.

Embodiment 2-4

COMPARATIVE EXAMPLE 1-2

Manipulating each of geraniol, nerol, perillaldehyde, isobornyl acetate and guaiac acetate for fragrance component in the same way as in Embodiment 1, each dual minimum inhibitory concentration of FIGS. 3-5 and FIGS. 9-10 was obtained. From the obtained result, the antibacterial effect was evaluated by the above-mentioned evaluation criterion. The result is shown in the table 1.

TABLE 1

| | fragrance component | E. coli | S. aureus | C. albicans | A. niger |
|---|---|---|---|---|---|
| Embodiment 1 | citral | ◯ | ◯ | ◯ | ◯ |
| Embodiment 2 | geraniol | ◯ | ◯ | ◯ | ◯ |
| Embodiment 3 | nerol | ◯ | ◯ | ◯ | ◯ |
| Embodiment 4 | perillaldehyde | ◯ | ◯ | ◯ | ◯ |
| Comparative example 1 | isobornyl acetate | X | ◯ | X | X |
| Comparative example 2 | guaiac acetate | X | ◯ | X | X |

Embodiment 5-7

Figure 6:
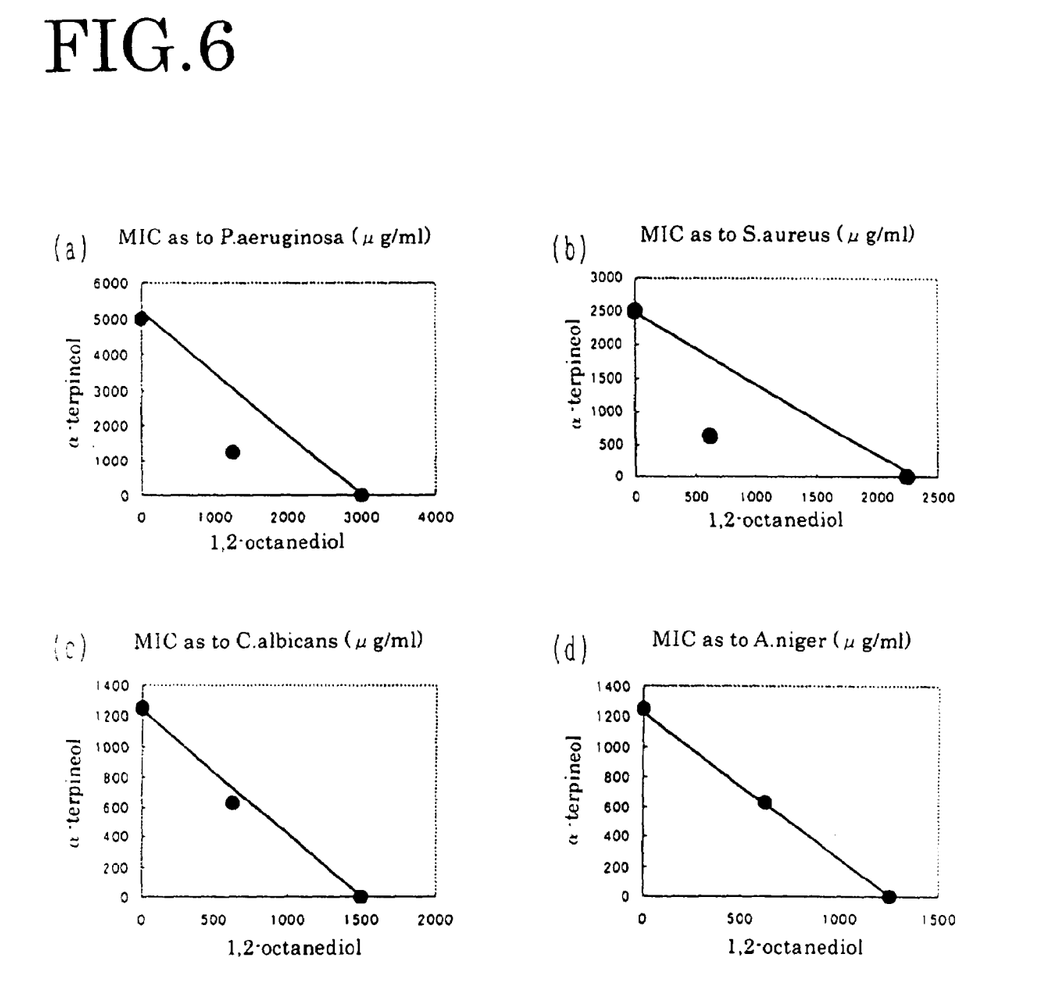
FIG. 6 is dual minimum inhibitory concentration diagrams as to α-terpineol.
Figure 7:
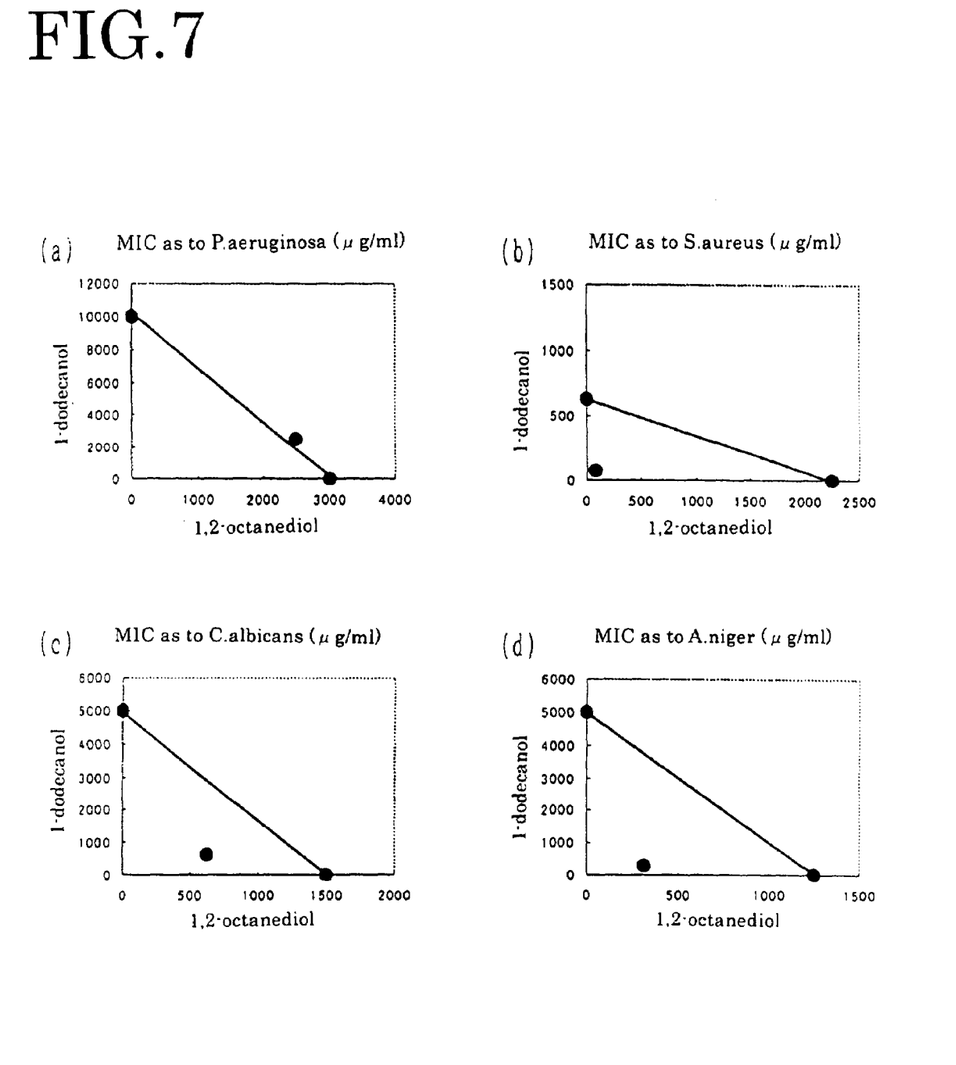
FIG. 7 is dual minimum inhibitory concentration diagrams as to dodecanol.
Figure 8:
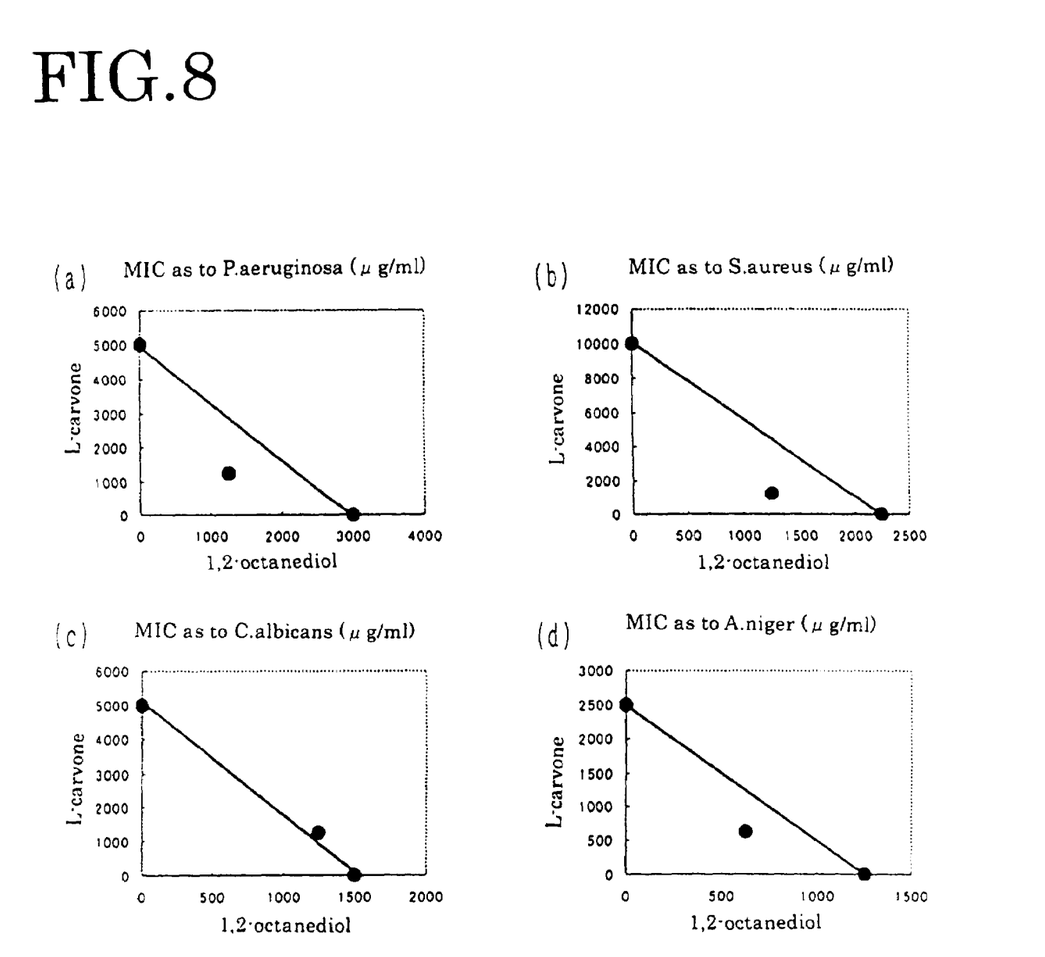
FIG. 8 is dual minimum inhibitory concentration diagrams as to L-carvone.
Figure 9:
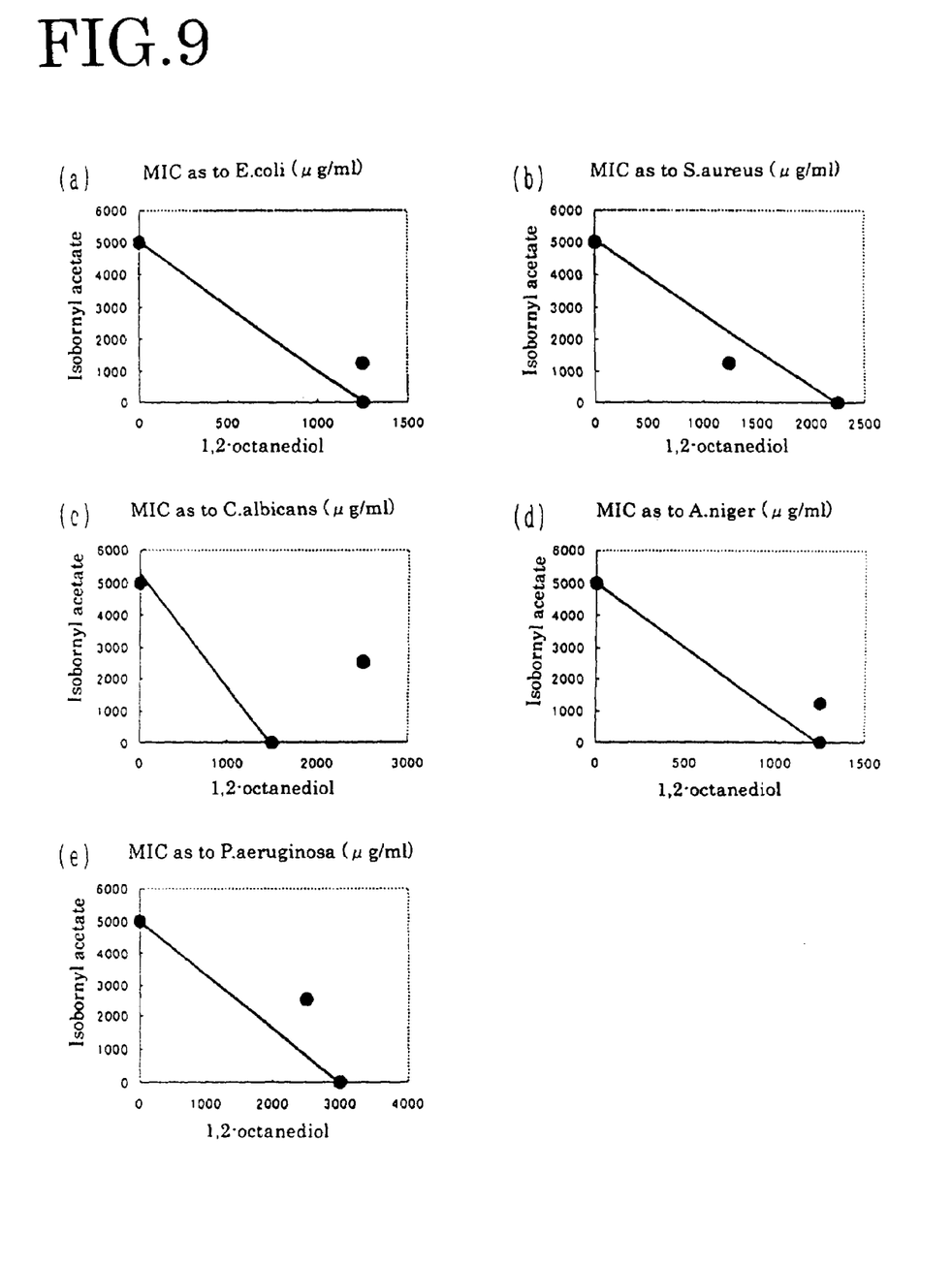
FIG. 9 is dual minimum inhibitory concentration diagrams as to isobornyl acetate.
Figure 10:
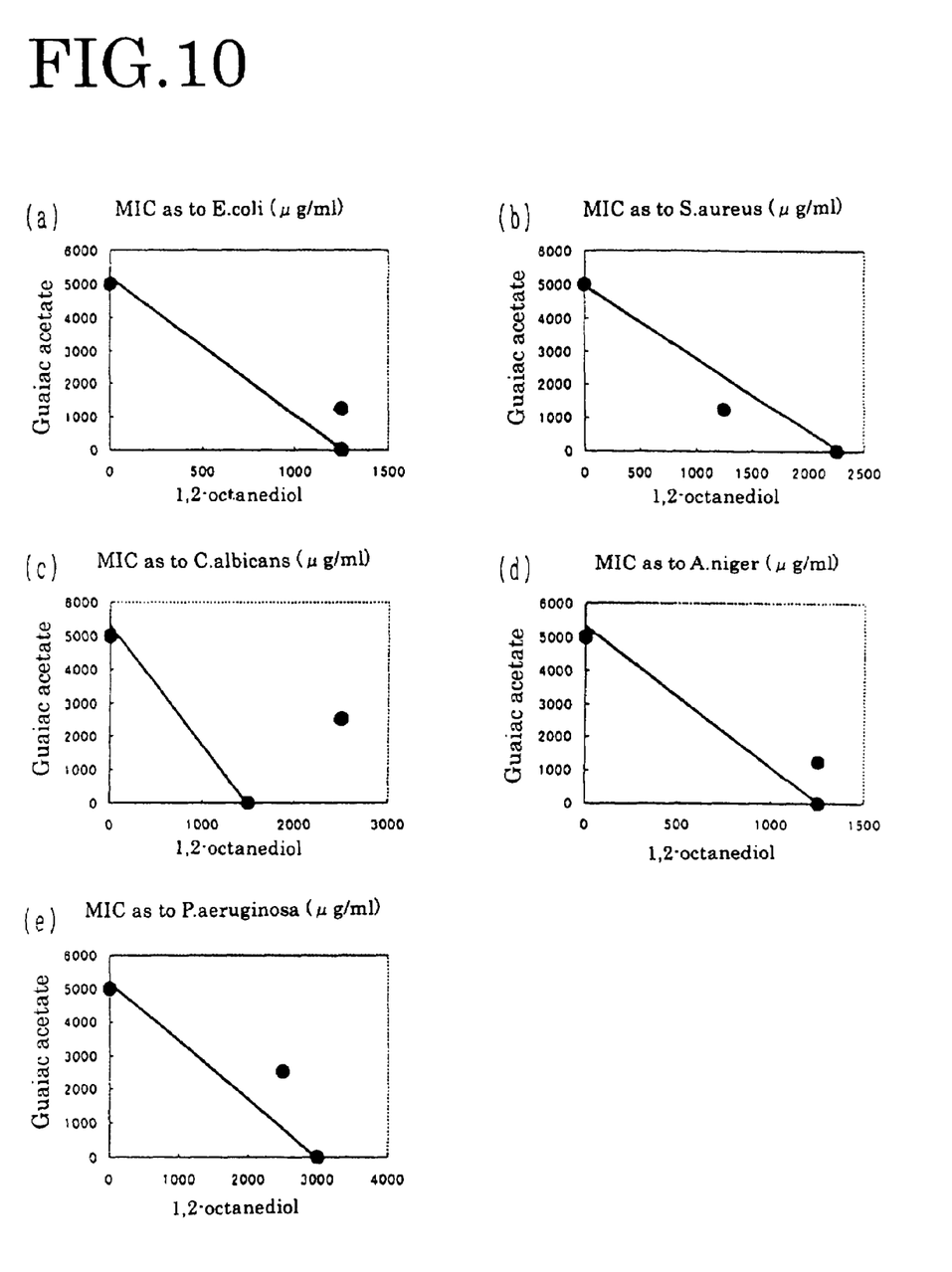
FIG. 10 is dual minimum inhibitory concentration diagrams as to guajac acetate.

Manipulating each of α-terpineol, 1-dodecanol, L-carvone for fragrance component in the same way as in Embodiment 1 using *Pseudomonas aeruginosa* IFO13275 as Gram-negative bacteria, each dual minimum inhibitory concentration of FIGS. 6-8 was obtained. Each dual minimum inhibitory concentration of isobornyl acetate and guaiac acetate against *Pseudomonas aeruginosa* was obtained in the same way. From the obtained result, the antibacterial effect was evaluated by the above-mentioned evaluation criterion. The result is shown in the Table 2.

TABLE 2

|  | fragrance component | P. aeruginosa | S. aureus | C. albicans | A. niger |
|---|---|---|---|---|---|
| Embodiment 5 | α-terpineol | ○ | ○ | ○ | Δ |
| Embodiment 6 | 1-dodecanol | Δ | ○ | ○ | ○ |
| Embodiment 7 | L-Carvone | ○ | ○ | Δ | ○ |
| Comparative example 1 | isobornyl acetate | X | ○ | X | X |
| Comparative example 2 | guaiac acetate | X | ○ | X | X |

From the result shown in the Tables 1 and 2, it can be known that it enhances the antibacterial activity which 1,2-alkanediol originally has against a broad range of strains to use 1,2-alkanediol in combination with a certain fragrance component such as citral, geraniol, nerol, perillaldehyde, α-terpineol, dodecanol and L-carvone.

On the other hand, it can be known that using 1,2-alkanediol in combination with other fragrance component such as isobornyl acetate or guaiac acetate does not enhance the antibacterial activity against a broad range of strains.

Examples of the compound of Antiseptic disinfectant, and cosmetics and toiletries, medicine or food containing the same according to the present invention are described as follows.

FORMULATION EXAMPLE 1

Humidity Retention Cream

| | |
|---|---|
| deca glyceryl monolaurate | 1.0 |
| POE (15) glyceryl monostearate | 1.0 |
| soybean phosphatide for hydrogenation | 1.0 |
| stearic acid | 4.0 |
| cetanol | 2.0 |
| behenyl alcohol | 2.0 |
| paraffin | 3.0 |
| squalane | 12.0 |
| jojoba oil | 4.0 |
| methyl polysiloxane | 0.2 |
| 1,3-butylene glycol | 3.0 |
| L-arginine | 0.1 |
| xanthan gum | 0.001 |
| 1,2-octanediol | 0.25 |
| citral | 0.1 |
| purified water | proper quantity |
| total | 100 percent by weight |

FORMULATION EXAMPLE 2

Hydrophilic Ointment

| | |
|---|---|
| ascorbic acid | 0.5 |
| polyoxyethylene cetyl ether | 2.0 |
| soybean phosphatide for hydrogenation | 1.0 |
| stearic acid | 4.0 |
| glyceric monostearate | 10.0 |
| liquid paraffin | 10.0 |
| Vaseline | 4.0 |
| cetanol | 5.0 |
| propylene glycol | 5.0 |
| 1,2-hexanediol | 0.5 |

| | |
|---|---|
| nerol | 0.2 |
| purified water | proper quantity |
| total | 100 percent by weight |

FORMULATION EXAMPLE 3

Beverage

| | |
|---|---|
| dextrose syrup | 33.0 |
| grapefruit juice | 64.0 |
| 1,2-pentanediol | 0.5 |
| perillaldehyde | 0.01 |
| fragrance | 0.5 |
| acidulant | proper quantity |
| total | 100 percent by weight |

EFFECT OF THE INVENTION

As disclosed above, the antiseptic disinfectant of the present invention enhances the antibacterial activity that 1,2-alkanediol originally have against a broad range of the strains. Accordingly, it is not necessary to compound the conventional antiseptic disinfectant, and high degree of safety can be obtained.

Further, when 1,2-hexanediol or 1,2-octanediol is used for 1,2-alkanediol, the antiseptic disinfectant with higher antibacterial activity can be obtained.

The cosmetics and toiletries, medicine or food of the present invention do not need to contain the conventional antiseptic disinfectant such as salicylic acid, benzoic acid or paraben, and the antiseptic disinfectant of the present invention has a excellent antibacterial activity. Accordingly, the compounding rate of the antiseptic disinfectant itself can be low, and the safety is extremely high.

INDUSTRIAL APPLICABILITY

The antiseptic disinfectant of the present invention enhances the antibacterial activity that 1,2-alkanediol originally have against a broad range of the strains, and has high degree of safety. Therefore, it can be suitably used as the antiseptic disinfectant for cosmetics and toiletries, medicine or food.

What is claimed is:

1. An antiseptic disinfectant containing synergistic effective amounts of 1,2-alkanediol with 5-10 carbons and one or more materials selected from the group consisting of citral, geraniol, nerol, perillaldehyde, α-terpineol, dodecanol and L-carvone wherein said 1,2-alkanediol is 1,2-octanediol.

2. Cosmetics and toiletries containing the antiseptic disinfectant described in claim 1.

3. Medicine containing the antiseptic disinfectant described in claim 1.

4. Food containing the antiseptic disinfectant described in claim 1.

* * * * *